(12) United States Patent
Sommazzi et al.

(10) Patent No.: US 6,780,947 B1
(45) Date of Patent: Aug. 24, 2004

(54) METAL COMPLEXES COMPRISING A 2,6-DIACYLPYRIDINE-LIGAND AND THEIR USE IN THE POLYMERIZATION OF ETHYLENE

(75) Inventors: Anna Sommazzi, Santa Margherita Ligure (IT); Barbara Milani, Gorizia (IT); Antonio Proto, Novara (IT); Gianni Corso, Carlino (IT); Giovanni Mestroni, Trieste (IT); Francesco Masi, Sant'Angelo Lodigiano (IT)

(73) Assignee: Enichem S.p.A., San Donato Milanese (IT)

( * ) Notice: Subject to any disclaimer, the term of this patent is extended or adjusted under 35 U.S.C. 154(b) by 57 days.

(21) Appl. No.: 10/048,921

(22) PCT Filed: Aug. 3, 2000

(86) PCT No.: PCT/EP00/07549

§ 371 (c)(1),
(2), (4) Date: Jun. 12, 2002

(87) PCT Pub. No.: WO01/10875

PCT Pub. Date: Feb. 15, 2001

(30) Foreign Application Priority Data

Aug. 5, 1999 (IT) .......................................... MI99A1764

(51) Int. Cl.[7] .............................. C08F 4/52; C08F 4/70
(52) U.S. Cl. ...................... 526/161; 526/172; 526/134; 526/169.1; 502/103; 502/117; 502/155; 502/167; 556/33; 556/34; 556/137; 556/138
(58) Field of Search ................................. 526/161, 172; 502/103, 117, 155, 167; 556/33, 34, 137, 138

(56) References Cited

FOREIGN PATENT DOCUMENTS

| WO | 98 27124 | | 6/1998 |
| WO | WO 00/20427 A1 | | 4/2000 |
| WO | WO 00/20427 | * | 4/2000 |

OTHER PUBLICATIONS

Austrian 1st Office Action Based on PCT/EP00/07549 (w/English Translation).

Emilia Luks et al.: "The template synthesis and characterization of new mono– and dinuclear podand Schiff base complexes of scandium group elements" Collect. Czech. Chem. Commun., vol. 63, No. 3, pp. 371–377.

* cited by examiner

*Primary Examiner*—Roberto Rabago
(74) *Attorney, Agent, or Firm*—Oblon, Spivak, McClelland, Maier & Neustadt, P.C.

(57) ABSTRACT

Organometallic complex having the formula $(IAP)M(X)_n$ which can be used for die formation of catalytic systems wherein: M is a metal selected from transition metals and lanthanides, in oxidation state "s" positive and different from zero; each X is independently a group of an anionic nature bound to the metal as an anion in an ionic couple or with a convalent bond of the "σ" type; "n" expresses the number of X groups sufficient for neutralizing the formal "+s" charge of the metal M, and (IAP) represents a neutral bond consisting of a mono-imine of 2,6-diacylpyridine. Said complex is prepared with relatively simple methods and can be used, combined with a suitable co-catalyst, such as for example, an aluminoxane, as a catalyst in normal (co)polymerization processes of α-olefins, and especially ethylene.

20 Claims, No Drawings

METAL COMPLEXES COMPRISING A 2,6-DIACYLPYRIDINE-LIGAND AND THEIR USE IN THE POLYMERIZATION OF ETHYLENE

The present invention relates to new metal complexes and their use in the preparation of catalytic compositions capable of polymerizing α-olefins.

More specifically, the present invention relates to a particular organometallic complex of a transition metal or of the group of lanthanides, a catalytic composition comprising it and at least one organometallic activator, as well as a process for the (co)polymerization of α-olefins within a wide range of temperatures and pressures, in the presence of said catalytic composition.

It is generally known in the art that ethylene, or α-olefins in general, can be polymerized or copolymerized by means of low, medium or high pressure processes with heterogeneous catalysts based on a transition metal of groups 4 to 6 of the periodic table of elements (in the form approved of by IUPAC and published by "CRC Press Inc." in 1989, to which reference will be made hereafter with the term "periodic table"), generally known as Ziegler-Natta type catalysts. A more recent group of catalysts active in the polymerization of α-olefins consists of the combination of an oligomeric organo-oxygenated derivative of aluminum (in particular methylaluminoxane or MAO) with an $\eta^5$-cyclopentadienyl compound (metallocene) of a transition metal of the same groups 4 to 6 of the periodic table, and especially group 4. These latter catalysts are substantially soluble in hydrocarbon solvents and for this reason are often defined as "homogeneous", even if used at times in heterogeneous form by means of supporting on an inert solid material. The characteristics of polymerization processes based on this type of catalytic systems can substantially differ from those of processes using heterogeneous catalysts of the Ziegler-Natta type, to such an extent that new olefinic polymers can be obtained, in certain cases, which could not be prepared with the traditional systems. Among the numerous publications available in literature on the matter, reference is made, for example, to the publications "Progress in Polymer Science", vol. 20 (1995), pages 309–367, and "Journal of Molecular Catalysis A: Chemical", vol. 128 (1998), pages 1–331, for a wide range of applications of the above techniques and results obtained.

In the continuous attempt to improve the state of the art, new catalysis methods have been recently proposed for the polymerization of α-olefins based on complexes of "heavy" transition metals, i.e. of groups 8 to 10 of the periodic table.

Oligomerization processes of olefins in the presence of nickel complexes have already been known for some time but it has rarely been possible to obtain high olefinic polymers with a catalysis based on this metal, as described, for example, in European patent 558,143.

Subsequently, international patent application WO 96/23010 described complexes of Pd(+2) or Ni(+2) with 1,4-N,N-1,4-diphenylbutadiene (DAB), or other ligands deriving therefrom, having the following characteristic structure (I):

(I)

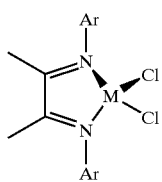

wherein each Ar group is a phenyl group optionally substituted with hydrocarbyl radicals, which, combined with typical activators of metallocene complexes, such as MAO mentioned above, or ionic activators more recently developed, based on boranes, are capable of homopolymerizing ethylene to surprisingly give a branched product, or co-polymerizing ethylene with other α-olefins, with non-conjugated dienes and with α,β-unsaturated polar organic compounds such as acrylates. In spite of a significant improvement with respect to the prior known art, the molecular weights obtained are still unsatisfactory. It has been observed, however, that with this group of catalysts, the molecular weight of the polyethylene produced increases with an increase in the steric hindrance of the substituents on the two aromatic groups bound to the nitrogen atoms.

Polymerization catalysts have also been proposed, according to international patent application WO 98/27124, comprising iron and cobalt complexes with nitrogenated tridentate chelating agents (TRI) having the following general formula (II):

(II)

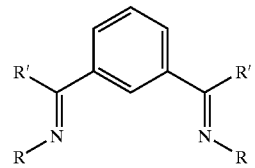

wherein each R—N generally consists of a derivative of aniline of the following type:

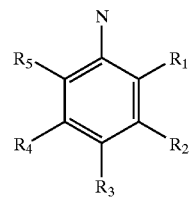

wherein the groups $R_1$ and $R_5$ groups are alkyl groups with a high steric hindrance, such as for example, iso-propyl, tert-butyl, etc., whereas $R_2$, $R_3$ and $R_4$ can be indifferently selected from hydrogen, alkyl, substituted alkyl, aryl. For example, the following two structures are provided for the preparation of cobalt or iron complexes suitable for the polymerization of ethylene:

(III)

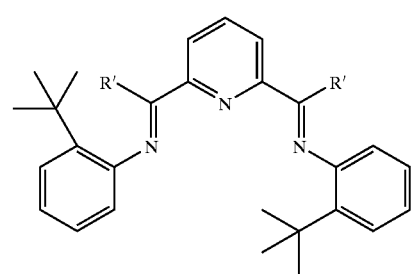

(IV)

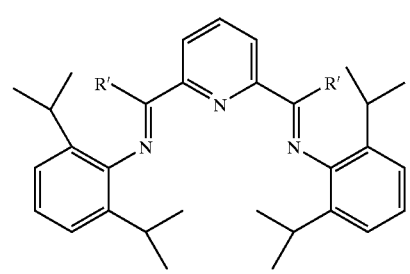

wherein: R'=H or $CH_3$.

These ligands can form catalysts having a certain polymerization activity also in situ, i.e. if charged into the polymerization reactor as such, in the presence of suitable Fe or Co metal salts. For example, it is described that by charging Co(acac)$_2$+(IV)+MAO (or MMAO) into a reactor in the presence of ethylene, the formation of polyethylene is observed even though there is a modest catalytic activity with respect to cobalt.

The molecular weight control of the polymer obtained with said catalysts critically depends on the steric hindrance of the $R_1$ and $R_5$ groups of each phenylimine group. Higher molecular weights are obtained with substituents with a greater hindrance. However, compared with those obtained with traditional catalytic systems, the olefinic polymers produced, under comparative conditions, with the above catalytic systems, still show decisively low, polydispersed molecular weights, which are such that the mechanical and process qualities required for typical market uses such as the production of films or plates, cannot be reached.

Another example is the publication "Collect. Czech. Chem. Commun." (vol. 63, no.3, 1998, pages 371–377) disclosing lanthanide complexes bearing an acyclic open-chain ligand obtained by condensation of 2 molecules of 2,6-diacetylpyridine with one molecule of 1,3-phenylenediamine, said ligand being therefore characterised by the presence of 2 imine functions together with 2 acyl functions.

Contrary to the current opinion that the presence of two phenylimine groups substituted with radicals having a high steric hindrance, is critical in the above ligands to obtain polymeric materials of α-olefins with a satisfactory molecular weight, the Applicant has surprisingly found that this requisite is not necessary for complexes with particular imine ligands defined and claimed hereunder. These complexes can also be obtained with simpler and more rapid methods than the complexes according to the above international patent application WO 98/27124, and are consequently more economic and available.

A first object of the present invention therefore relates to a complex of a metal M selected from transition metals and lanthanides in an oxidation state different from zero, comprising a neutral ligand coordinated to the metal M consisting of a mono-imine of 2,6-diacylpyridine (abbreviated IAP) having the following general formula (V):

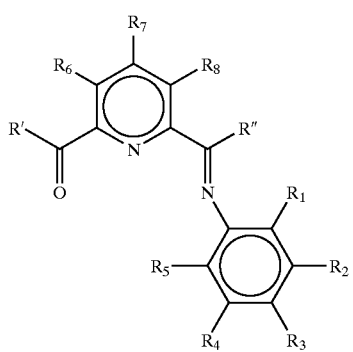

(V)

wherein: R' and R" can be independently hydrogen or a hydrocarbon radical, preferably aliphatic, having from 1 to 10 carbon atoms, optionally halogenated, more preferably methyl, each $R_i$ (i=1–8) is independently hydrogen, halogen or $C_1$–$C_{10}$ alkyl, or $C_6$–$C_{15}$ aryl, optionally halogenated, on the condition that at least one of the $R_1$ or $R_5$ groups, preferably both, is a hydrocarbon radical.

Said complex as defined in accordance with the present invention comprises any physical form thereof, such as for example, its isolated solid form, the form dissolved in a suitable solvent, or supported on appropriate organic or inorganic solids, preferably having a granular or powder physical form. In general, it can be represented, in the terms specified above, by the following formula (VI):

$$(IAP)M(X)_n \qquad (VI)$$

wherein: (IAP) represents the above ligand having formula (V),

M is a metal selected, in its more general sense, from transition metals, i.e. metals of groups 3 to 12 of the periodic table, and from lanthanides, which is in an oxidation state "s" positive and different from zero, generally ranging from 1 to 4, depending on the metal M in question, and preferably equal to one of the so-called "metallic" oxidation states specified in the periodic table mentioned above;

each X is independently a group of an anionic nature bound to the metal as anion in an ionic couple or with a covalent bond of the "σ" type; and "n" expresses the number of X groups sufficient for neutralizing the formal "s" oxidation charge of the metal M, and is equal to "s" if all the X groups are monovalent.

In the previous definition of the complex having formula (VI) and hereinafter in the present description, the following terms are used with the meaning specified below:

"metallic" with reference to the oxidation state, defines oxidation states in which the metal can exist as an ion, unlike "non-metallic" oxidation states of transition metals such as, for example, Cr(+6), V(+5) or Re(+8), which, as is known, do not exist in nature as ions with this charge, but are generally bound to O, S, F atoms and other strongly electro-negative elements;

"(co)polymerization", with reference to α-olefins, comprises both the homo-polymerization and the co-polymerization of ethylene and/or other α-olefins with more than two carbon atoms, with each other or with another ethylenically unsaturated polymerizable compound;

"co-polymer of", when referring to a certain α-olefin, means that said copolymer contains at least 20% in moles of monomeric units deriving from said α-olefin;

"polydentate" or "polyvalent", with reference to a substituent group, an ion, a ligand, an organic radical, indicates the presence of at least two functions, interactions, bonds or valences.

In accordance with the present invention, preferred complexes having formula (VI) are those in which the metal M is selected from metals of groups 4 to 10 of the periodic table. Particularly significant results in the (co)polymerization of α-olefins have been obtained with metals of groups 8 and 9, especially with cobalt, iron, ruthenium, rhodium and iridium in oxidation states +2 and +3. Cobalt and iron in oxidation state +2 are particularly suitable.

The symbol X in formula (VI) indicates groups (or ligands) of an ionic nature of the complex claimed. It is known that transition metals and lanthanides rarely form compounds and complexes of an exclusively ionic nature, as in many cases, the bond between metal and ligand is of an ionic-covalent or totally covalent nature. The symbol X in formula (VI) therefore indicates ligands of an anionic nature, which are normally bound to the metal M with a bond mainly of a covalent nature. The term $(X)_n$ generally indicates the combination of bonds of an anionic nature, regardless of the effective number and type of X present in the compound having formula (VI). Different X ligands are included in the above definition. Polyvalent or polydentate $(X)_n$ ligands are also included in the scope of the present invention, such as for example, in the case of oxalate, sulfate or phthalate groups.

Examples of groups of $(X)_n$ ligands of an anionic nature which can form compounds having formula (VI) are halides, especially chloride and bromide, sulfates, and acid sulfates, alkyl- and aryl-sulfonic groups, phosphates and polyphosphates, alkyl- and aryl-phosphonic groups, hydride, linear, cyclic or branched alkyl groups having from 1 to 15 carbon atoms, such as methyl, ethyl, butyl, isopropyl, isoamyl, octyl, decyl, benzyl, cyclopentyl, cyclohexyl, 4-methylcyclohexyl, alkylsilyl groups having from 1 to 20 carbon atoms, such as for example, trimethylsilyl, triethylsilyl or tributylsilyl, aryl groups having from 6 to 15 carbon atoms, such as phenyl or toluyl, alkoxyl or thioalkoxyl groups having from 1 to 10 carbon atoms, such as methoxyl, ethoxyl, iso- or sec-butoxyl, ethylsulfide, carboxylate or dicarboxylate groups, such as acetate, trifluoroacetate, propionate, butyrate, pivalate, stearate, benzoate, oxalate, malonate, phthalate, and preferably carboxylate or dicarboxylate groups having from 1 to 10 carbon atoms, or again, a dialkylamide group having from 2 to 15 carbon atoms, such as diethylamide, dibutylamide, or alkylsilyl-amide, such as bis(trimethylsilyl)amide or ethyltrimethylsilylamide, divalent organic groups such as trimethylene or tetramethylene, or ethylenedioxy groups.

Groups or ligands different from each other, if desired, can also be present, such as for example, a chloride and a carboxylate or alkoxide group. The X groups are preferably selected so that the complex having formula (VI) is sufficiently soluble in the solvents used during the polymerization process, especially in the case of solution processes. In certain cases however the solubility of the complex is irrelevant, as in the case of supported complexes. In this latter case, the group of an anionic nature (X) can also have an anionic function chemically bound to the carrier.

To facilitate the production and conservation of the respective complexes, chorine, bromine, alkoxide and carboxylate groups (having from 2 to 15 carbon atoms) are preferred X groups.

According to what is specified above, the polydentate ligand identified by the abbreviation "IAP" in formula (VI) is a mono-imine of 2,6-diacylpyridine, having the above general formula (V). In this formula the different $R_i$ groups (i=1, . . . , 8) and R', R", are normally hydrogen, halogen or hydrocarbon groups having from 1 to 15 carbon atoms. In the case of hydrocarbon groups, substituted groups are not excluded from the scope of the present invention, provided they have functions incapable of chemically reacting (substantially inert, for example, halogens) with the components of the catalytic systems comprising said complexes having formula (VI) and the processes catalyzed thereby.

Whereas a wide range of possible R substituents is available to experts in the field, it is critical, for the purposes of the present invention, for at least one group selected from $R_1$ and $R_5$ to be a hydrocarbyl radical, preferably branched alkyl such as isopropyl, s-butyl, t-butyl or benzyl, or aryl such as phenyl or 4-methylphenyl, to give the imine substituent the necessary steric hindrance which determines its space configuration. These radicals are preferably hydrocarbon groups having from 1 to 10 carbon atoms, and can be, for example, methyl, s-butyl, isopropyl, ter-butyl, cyclohexyl, phenyl, or benzyl. These radicals are more preferably both methyl or isopropyl, or one of them is hydrogen and the other, for example, ter-butyl. These radicals are also more preferably both methyl or ethyl groups or at least one of them is a branched alkyl group having from 3 to 10 carbon atoms.

The radicals $R_2$, $R_3$ and $R_4$ or the imine group having formula (V) preferably independently represent an aliphatic alkyl group having from 1 to 4 carbon atoms, and are more preferably all methyl or hydrogen.

The groups R' and R" are preferably alkyl groups having from 1 to 5 carbon atoms, preferably methyl.

According to a particular aspect included in the scope of the present invention, adjacent $R_1$ groups can be optionally further chemically bound to each other to form a cyclic structure joined to the aromatic ring of the imine group.

The ligands having formula (V) can be prepared using, as precursor, a diacylpyridine with a suitable structure, in particular having the pre-selected substituent groups corresponding to groups R', R", $R_6$, $R_7$ and $R_8$ in formula (V) of the desired ligand. Said diacylpyridine is reacted, preferably in a solution of an inert organic liquid, preferably selected from halogenated hydrocarbons, aromatic hydrocarbons, ethers, esters, amides, alcohols, with an aniline substituted on positions 1 to 5 of the ring corresponding to groups $R_1$, $R_2$, $R_3$, $R_4$ and $R_5$ in the compound having formula (V) to be obtained, in the presence of a protic acid, preferably a carboxylic acid, as reaction catalyst. The reaction is carried out at temperatures generally ranging from 0 to 60° C., preferably from 20 to 40° C., using molar ratios of around 1/1 between the reagents. It has been observed however, that it is also possible to obtain the desired mono-imine having formula (V) using aniline/diacylimine ratios greater than 1/1, and up to 2/1 and over, operating under temperature conditions ranging from 0 to 40° C. and for times of up to 5 hours, whereas this does not occur when non-substituted aniline is used. The conditions generally preferred for carrying out the synthesis are aniline/diacylimine molar ratios ranging from 1.05 to 1.30, temperatures ranging from 0 to 40° C., reaction times of 1 to 24 hours, more preferably from 1 to 8 hours, in an alcohol as solvent (preferably methanol or ethanol) and in the presence of a carboxylic acid in a molar ratio ranging from 0.1 to 0.5 with respect to the diacylpyridine. The compound having formula (V) is then separated and purified applying normal methods of organic chemistry suitable for the purpose.

The compound having formula (V) is in turn an intermediate in the preparation of the above metal complexes having formula (VI), in which it is present in a form coordinated to the metal M.

According to the present invention, the complex having formula (VI) can be prepared by means of a simple and convenient process comprising contact and reaction, preferably in the presence of an inert liquid to facilitate molecular migration, of the above IAP ligand having formula (V) with a salt of the metal M selected. For example, it is possible to start from the chloride of the metal M dissolved in an alcohol, such as butanol, or a polar ether, such as tetrahydrofuran (THF), by the addition of the stoichiometric quantity of the pre-selected ligand, and separation of the complex formed according to one of the normal methods known in the art such as, for example, crystallization or precipitation by means of a non-solvent, followed by separation by filtration or decanting. Owing to the great affinity of the compound having formula (V) for forming complexes with transition metals and lanthanides, the desired complex having formula (VI) is rapidly formed and with substantially quantitative yields already under bland temperature conditions. The following reaction scheme can be applied:

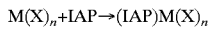

$$M(X)_n + IAP \rightarrow (IAP)M(X)_n$$

wherein the various symbols have the same meaning defined above for formula (VI).

The salt $M(X)_n$ can be any suitable salt of the metal M, or, if desired, a mixture of salts, also of different metals when a mixture of complexes having formula (VI) of different metals is desired. The most interesting results have been obtained with salts of metals of group 8 or 9 of the periodic table of elements. Typical salts suitable for the purpose are halides, especially chlorides and bromides, alcoholates, carboxylates, acetylacetonates, malonates, and analogous organic salts. Inorganic salts, however, such as carbonates and bicarbonates, etc. are also suitable for the purpose provided they are capable, according to what is known in inorganic chemistry, of interacting with the compound (IAP) in the reaction environment in order to form a coordination complex. Salts in which M and X are those specified above, in general and in the preferred form, with reference to the complex having formula (VI), are particularly suitable for the purposes of the present invention.

Said complexes having formula (VI), however, can also be obtained by modifying a pre-existing different complex having formula (VI), for example, by means of the exchange of a ligand of an anionic nature with another. Of particular interest for the present invention, is the method for the preparation of complexes having formula (VI) in which at least one X, and preferably two Xs, are alkyl groups having from 1 to 10, preferably from 1 to 5, carbon atoms, starting from the corresponding complexes having formula (VI) wherein X is, for example, chloride, alkoxide, amide or carboxylate, by alkylation with a suitable alkylating compound selected from known compounds suitable for this purpose, for example, a magnesium alkyl, a magnesium alkylhalide, an aluminum alkyl or an aluminum alkylhalide.

This preparation method, as also the previous one, can in certain cases also be used in situ directly in the environment destined for the polymerization process of which the complex having formula (VI) is a component of the catalytic system. This possibility forms a further advantageous aspect of the present invention, as is described in detail hereunder.

A further object of the present invention relates to a catalytic system for the (co)polymerization of (α-olefins comprising at least the following two components, as such or combined with each other:

(A) a complex of a metal M selected from transition metals and lanthanides, preferably selected from metals of groups 8 and 9 of the periodic table of elements, particularly Fe, Co, Ru, Ir and Rh, defined by the previous formula (VI);

(B) a co-catalyst consisting of at least one organic compound of an element M', different from carbon, selected from the elements of groups 2, 12, 13 or 14 of the periodic table as defined above.

In particular, according to the present invention, said element M' is selected from boron, aluminum, zinc, magnesium, gallium and tin, more particularly boron and aluminum.

In a preferred embodiment of the present invention, component (B) is an organo-oxygenated derivative of aluminum, gallium or tin. This can be defined as an organic compound of M', in which the latter is bound to at least one oxygen atom and to at least one organic group consisting of an alkyl group having from 1 to 6 carbon atoms, preferably methyl.

According to this aspect of the invention, component (B) is more preferably an aluminoxane. As is known, aluminoxanes are compounds containing Al—O—Al bonds, with a varying O/Al ratio, obtained in the art by reaction, under controlled conditions, of an aluminum alkyl, or aluminum alkyl halide, with water or other compounds containing pre-determined quantities of water available, as for example, in the case of the reaction of aluminum trimethyl with aluminum sulfate hexahydrate, copper sulfate pentahydrate or iron sulfate pentahydrate. Aluminoxanes which are preferably used for the formation of the polymerization catalyst of the present invention are cyclic and/or linear, oligo- or polymeric compounds, characterized by the presence of repetitive units having the following formula:

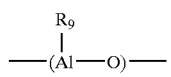

wherein $R_9$ is a $C_1$–$C_6$ alkyl group, preferably methyl.

Each aluminoxane molecule preferably contains from 4 to 70 repetitive units which are not necessarily all the same, but may contain different $R_9$ groups.

Said aluminoxanes, and particularly methylaluminoxane are compounds which can be obtained with known organometallic chemical processes, for example by the addition of aluminum trimethyl to a suspension in hexane of aluminum sulfate hydrate.

When used for the formation of a polymerization catalyst according to the present invention, the aluminoxanes are put in contact with a complex having formula (VI) in such proportions that the atomic ratio between Al and the transition metal M is within the range of 10 to 10,000 and preferably from 100 to 5,000. The sequence with which component (A) and the aluminoxane (B) are put in contact with each other, is not particularly critical.

In addition to the above preferred aluminoxanes, the definition of component (B) according to the present invention also comprises galloxanes (in which, in the previous formulae, gallium is present instead of aluminum) and stannoxanes, whose use as cocatalysts for the polymerization of olefins in the presence of metallocene complexes is known, for example, from U.S. Pat. Nos. 5,128,295 and 5,258,475.

According to another preferred aspect of the present invention, said catalyst can be obtained by putting component (A) consisting of at least on complex having formula (VI), in contact with component (B) consisting of at least one compound or a mixture of organometallic compounds of M', in particular boron, capable of reacting with the complex having formula (VI), extracting from this a σ-bound group X as defined above, to form, on the one hand at least one neutral compound, and on the other hand an ionic compound consisting of a cation containing the metal M coordinated to the ligand IAP, and an organic non-coordinating anion containing the metal M', in particular boron, whose negative charge is delocalized on a multicentric structure.

Components (B) suitable as ionizing systems of the above type are preferable selected form voluminous organic compounds of aluminum and especially of boron, such as for example, those represented by the following general formulae:

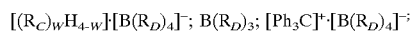
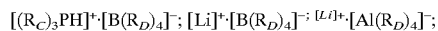

wherein the deponent "w" is an integer ranging from 0 to 3, each $R_C$ group independently are represents an alkyl or aryl radical having from 1 to 10 carbon atoms and each $R_D$ group independently represents an aryl radical partially or, preferably, totally fluorinated, having from 6 to 20 carbon atoms.

Said compounds are generally used in such quantities that the ratio between the atom M', in particular boron, in component (B) and the atom M in the complex having formula (VI) is within the range of 0.1 to 15, preferably from 0.5 to 10, more preferably from 1 to 6.

Component (B) can consist of a single compound, normally an ionic compound, or, especially when no X in the compound having formula (VI) is an alkyl, a combination of this compound with an alkylating agent such as MAO, or, preferably, with an aluminum trialkyl having from 1 to 8 carbon atoms in each alkyl residue, such as for example $AlMe_3$, $AlEt_3$, $Al(i-Bu)_3$, or consisting of aluminum alkyl or an according to what is specified above.

In general, the formation of the ionic-type catalytic system, in accordance with this latter aspect of the present invention, is preferably carried out in an inert liquid medium, more preferably hydrocarbon. The selection of components (A) and (B), which are preferably combined with each other, as well as the particular method used, can vary depending on the molecular structures and result desired, according to what is analogously described in specific literature available to experts in the field for other complexes of transition metals with imine ligands, for example by L. K. Johnson et al. in the publication "Journal of the American Chemical Society, vol. 117 (1995), pages 6414–6415, and by G. van Koten and K. Vrieze in "Advances in Organometallic Chemistry, vol. 21, page 151".

Examples of these methods are qualitatively schematized in the list provided hereunder, which however does not limit the overall scope of the present invention:

($m_1$) by contact of a complex having the previous general formula (VI), wherein at least one ligand X is hydrogen or an alkyl radical, with an ionic compound whose cation is capable of reacting with one of said substituents to form a neutral compound, and whose anion is voluminous, non-coordinating and capable of delocalizing the negative charge;

($m_2$) by the reaction of a complex having the previous formula (VI) with an alkylating agent, preferably an aluminum trialkyl, used in molar excess of 10/1 to 300/1, followed by the reaction with a strong Lewis acid, such as for example, tris(pentafluoro-phenyl) boron a in more or less stoichiometric quantity or in slight excess with respect to the metal M;

($m_3$) by contact and reaction of a complex having the previous formula (VI) with a molar excess of 10/1 to 1000/1, preferably from 100/1 to 500/1 of an aluminum trialkyl or an alkylaluminum halide represented by the formula $AlR'''_m Z_{3-m}$, wherein: R''' is a linear or branched $C_1$–$C_8$ alkyl group, or one of their mixtures, Z is a halogen, preferably chlorine or bromine, and "m" is a decimal number ranging from 1 to 3;

followed by the addition to the composition thus obtained, of at least one ionic compound of the type described above in such quantities that the ratio between B or Al in the ionic compound and the atom M in the complex having formula (V) is within the range of 0.1 to 15, preferably from 1 to 6.

Examples of ionizing ionic compounds or multi-component reactive systems capable of producing an ionic catalytic system by reaction with a complex having formula (VI) according to the present invention, are described, although with reference to the formation of ionic metallocene complexes, in the following publications, whose content in herein incorporated as reference:

W. Beck et al., Chemical Reviews, Vol. 88 (1988), pages 1405–1421;

S. H. Stares, Chemical Reviews, Vol. 93 (1993), pages 927–942;

Published European patent applications Nr.: EP-A 277.003, EP-A 495,375, EP-A 520,732, EP-A 427,697, EP-A 421,659, EP-A 418,044;

Published international patent applications Nr.: WO 92/00333, WO 92/05208.

It has been found that the behaviour and reactivity of these ionic activator systems towards complexes having formula (VI) is essentially analogous to that observed in the case of metallocene complexes of Ti and Zr used as catalysts in the polymerization of olefins. The specific characteristics of the catalytic system in accordance with the present invention should therefore be considered as being essentially due to the presence of the complex having formula (VI), or to the products deriving therefrom during the formation of the activated catalytic system.

Also included in the scope of the present invention are those catalytic systems comprising two or more complexes having formula (VI) mixed with each other. Catalysts of the present invention based on mixtures of complexes having different catalytic activities can be advantageously used in polymerization when a wider molecular weight distribution of the polyolefins thus produced, is desired.

According to another aspect of the present invention, in order to produce solid components for the formation of catalysts for the polymerization of olefins, the above complexes can also be supported on inert solids, preferably consisting of oxides of Si and/or Al, such as, for example, silica, alumina or silico-aluminates. For the supporting of said catalysts, the known supporting techniques can be used, normally comprising contact, in a suitable inert liquid medium, between the carrier, optionally activated by heating to temperatures exceeding 200° C., and one or both of components (A) and (B) of the catalytic system of the present invention. For the purposes of the present invention, it is not necessary for both components to be supported, as it is also possible for only the complex having formula (VI), or the organic compound of B, Al, Ga or Sn as defined above, to be present on the surface of the carrier. In the latter case, the component which is not present on the surface is subsequently put in contact with the supported component, at the moment of the formation of the catalyst active for the polymerization.

Also included in the scope of the present invention are the complexes, and catalytic systems based on these, which have been supported on a solid by means of the functionalization of the latter and formation of a covalent bond between the solid and a complex included in the previous formula (VI).

One or more other additives or components can be optionally added to the catalytic system according to the present invention, as well as the two components (A) and (B), to adapt it for satisfying specific requisites. The catalytic systems thus obtained should be considered as being included in the scope of the present invention. Additives or components which can be included in the preparation and/or formulation of the catalyst of the present invention are inert solvents such as, for example, aliphatic and/or aromatic hydrocarbons, aliphatic and aromatic ethers, weakly coordinating additives (Lewis bases) selected, for example, from non-polymerizable olefins and sterically hindered or electronically poor ethers, halogenating agents such as silicon halides, halogenated hydrocarbons, preferably chlorinated, and the like.

Components (A) and (B) form the catalyst of the present invention by contact with each other, preferably at temperatures ranging from 20 to 60° C. and for times varying from 10 seconds to 10 hours, more preferably from 30 seconds to 5 hours.

As mentioned above, the catalytic system according to the present invention is suitable, in its most general sense, for effecting any (co)polymerization process of α-olefins, which in turn forms an object of the present invention. This can be carried out with satisfactory results with any combination of conditions normally used in polymerization processes of α-olefins, owing to the specific activity and long duration of the catalytic system used.

The catalytic systems according to the present invention can be used with excellent results in substantially all known (co)polymerization processes of α-olefins, either in continuous or batchwise, in one or more steps, such as, for example, processes at low (0.1–1.0 MPa), medium (1.0–10 MPa) or high (10–150 MPa) pressure, at temperatures ranging from 20° to 250° C., optionally in the presence of an inert diluent, at least one olefin being put under the above conditions in contact with the above catalytic system. Hydrogen can be conveniently used as molecular weight regulator.

These processes can be carried out in solution or suspension in an inert liquid diluent normally consisting of an aliphatic or cycloaliphatic or aromatic hydrocarbon, having from 3 to 8 carbon atoms, but which can also consist of a monomer as, for example, in the known co-polymerization process of ethylene and propylene in liquid propylene. The α-olefins to be polymerised can comprise from 2 to 20 carbon atoms. The quantity of catalyst introduced into the polymerization mixture is preferably selected so that the concentration of the transition metal M ranges from $10^{-4}$ to $10^{-8}$ moles/liter.

Alternatively, the polymerization can be carried out in gas phase, for example, in a fluid bed reactor, normally at pressures ranging from 0.5 to 5 MPa and at temperatures ranging from 50 to 150° C.

According to a particular aspect of the present invention, the catalytic system for the (co)polymerization of α-olefins is prepared separately (preformed) by contact of components (A) and (B), and is subsequently introduced into the polymerization environment. The catalytic system can be charged first into the polymerization reactor, followed by the reagent mixture containing the olefin or mixture of olefins to be polymerized, or the preformed catalytic system can be charged into the reactor already containing the reagent mixture or, finally, the reagent mixture and the catalytic system can be contemporaneously fed into the reactor.

According to another aspect of the present invention, the catalyst is; formed "in situ", for example by introducing components (A) and (B) separately into the polymerization reactor containing the pre-selected olefinic monomers and possible non-olefinic co-monomers. The use of this latter formation technique of the catalytic system should be appropriately evaluated by experts in the field to ensure that the contemporaneous presence of certain components reactive with each other, does not lead to results which are different from those expected.

For example, the in situ preparation technique is suitable when component (A) is a preformed complex having formula (VI) and component (B) is an organo-oxygenated compound of a metal of group 13, in particular an aluminoxane. Equally convenient, in terms of rapidity and facility for the preparation of the catalytic system, is the use of the in situ technique by the mixing, either contemporaneously or, preferably, in two subsequent steps, in the same reaction environment, of the IAP ligand having formula (V), a suitable salt of the metal $M(X)_n$ and aluminoxane, in the relative quantities specified above. The contact and reaction between a IAP ligand, a salt of the metal M and an aluminum alkyl, or other alkylating agent, followed by the addition of a non-coordinating ionizing compound, for the preparation in situ of an ionic catalytic system in accordance with the present invention, according to one of the general methods previously defined by "$m_2$" and "$m_3$", have proved to be less advantageous in certain cases, in terms of catalytic activity. In this case, it is preferable to perform the complex having formula (VI) to be subsequently used for the optional preparation in situ by reaction with an aluminum alkyl (or other alkylating agent) and an ionizing compound.

The catalysts according to the present invention can be used with excellent results in the polymerization of ethylene to give linear polyethylene and in the copolymerization of ethylene with propylene or higher α-olefins, preferably having from 4 to 10 carbon atoms, to give copolymers having different characteristics depending on the specific polymerization conditions and on the quantity and structure of the α-olefin. For example, linear polyethylenes can be obtained, with a density ranging from 0.880 to 0.940, and with molecular weights ranging from 10,000 to 2,000,000. The α-olefins preferably used as comonomers of ethylene in the production of low or medium density linear polyethylene (known with the abbreviations ULDPE, VLDPE and LLDPE depending on the density), are 1-butene, 1-hexene and 1-octene.

The catalyst of the present invention can also be conveniently used in copolymerization processes of ethylene and propylene to give saturated elastomeric copolymers vulcanizable by means of peroxides and extremely resistant to aging and degradation, or in the terpolymerization of ethylene, propylene and a non-conjugated diene, having from 5 to 20 carbon atoms, to obtain vulcanizable rubbers of the EPDM type. In the case of these latter processes, it has been found that the catalysts of the present invention allow the production of polymers having a particularly high diene content and average molecular weight, under the polymerization conditions.

According to a particular aspect of the present invention, the above (co)polymerization process is also suitable for the copolymerization of α-olefins, and ethylene in particular, with non hydrocarbon polymerizable unsaturated monomers, such as for example, esters of acrylic and methacrylic acid.

The catalysts of the present invention can also be used in homo- and co-polymerization processes of α-olefins having at least 3 carbon atoms, according to the known techniques, giving, with excellent yields, atactic, isotactic or syndiotactic polymers, depending on the nature of the complex having formula (VI) and type of monomer. α-olefins suitable for the purpose are those having from 3 to 20 carbon atoms, optionally also comprising halogens or aromatic nuclei such as, for example, propylene, 1-butene, 1-hexene, 4-methyl-1-pentene, 1-decene and styrene.

The present invention is further described by the following examples, which, however, are provided for purely illustrative purposes and do not limit the overall scope of the invention itself.

EXAMPLES

The analytical techniques and characterization methods used in the following examples are listed below and are briefly described.

The $^1$H-NMR spectra were registered by means of a nuclear magnetic resonance spectrometer mod. Bruker MSL-300, using $CDCl_3$ as solvent for each sample.

The measurement of the molecular weights of the olefinic polymers was carried out by means of Gel-Permeation Chromatography (GPC). The analyses of the samples were effected in 1,2,4-trichlorobenzene (stabilized with Santonox) at 135° C. with a WATERS 150-CV chromatograph using a Waters differential refractometer as detector.

The chromatographic separation was obtained with a set of $\mu$-Styragel HT columns (Waters) of which three with pore dimensions of $10^3$, $10^4$, $10^5$ Å respectively, and two with pore dimensions of $10^6$ Å, establishing a flow-rate of the eluant of 1 ml/min.

The data were obtained and processed by means of Maxima 820 software version 3.30 (Millipore); the number ($M_n$) and weight ($M_w$) average molecular weight calculation was carried out by universal calibration, selecting polystyrene standards with molecular weights within the range of 6,500,000–2,000, for the calibration.

The determination of the structures by means of X-rays of the new complexes according to the present invention was effected on a Siemens AED diffractometer.

During the preparations described in the examples, the following commercial reagents were used:

| | |
|---|---|
| 2,6-diacetylpyridine | FLUKA |
| 2,6-di-isopropyl aniline | ALDRICH |
| 2-tert-butyl aniline | ALDRICH |
| mesitylaniline | ALDRICH |
| methyllithium (MeLi) 1 M in diethyl ether | ALDRICH |
| butyllithium (BuLi) 2.5 M in hexane | ALDRICH |
| methylalumoxane (MAO) (Eurecene 5100 10T, 10% by weight of Al in toluene) | WITCO |

The reagents and/or solvents used and not indicated above are those commonly used both in bench and on industrial scale and can be easily found at all commercial operators specialized in the field.

Example 1 (Comparative)
preparation of: 2,6-diacetylpyr-idine-bis(phenylimine)

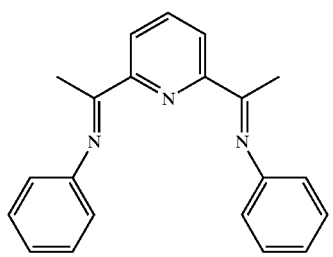

2.10 ml of aniline (0.023 moles), 5 ml of methanol and 0.25 ml of formic acid are charged into a glass flask. A limpid solution is formed to which 1.93 g of 2,6-diacetylpyridine (0.012 moles) dissolved in 20 ml of methanol are added dropwise at room temperature. After about 1 hour of reaction, a yellow microcrystalline solid is recovered by filtration, which is washed with cold methanol and dried under vacuum at room temperature.

1.81 g of a product are obtained which proves to be the desired compound, on the basis of the following characterization:

| Elemental analysis | | | |
|---|---|---|---|
| Elements | C % | H % | N % |
| Calculated for $C_{21}H_{19}N_3$ (MW = 313.4) | 80.5 | 6.11 | 13.4 |
| Experimental | 80.9 | 6.13 | 13.6 |

IR spectrum: the band of the carbonyl group of 2,6-diacetylpyridine centered at 1700 cm$^{-1}$ is absent, whereas the band at 1632 cm$^{-1}$ attributed to the $v_{C=N}$ vibration, is present.

Example 2
preparation of 1-{6-[2,6-diisopropylphenyl)-ethaneimidoyl]-2-pyridinyl}-1-ethanone (VII) with a ratio aniline/pyridine≅2.

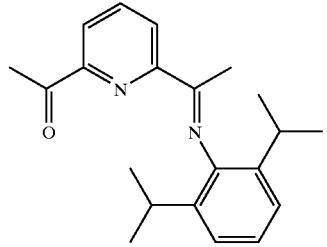

(VII)

The same procedure is adopted as in the previous example 1, with the only difference that 4.34 ml of 2,6-diisopropyl aniline (0.023 moles) are used instead of 2.10 ml of aniline.

At the end 2.53 g of a light yellow solid are obtained (m.p. =186–187° C.), corresponding to the desired product (VII), on the basis of the following characterization:

| Elemental analysis | | | |
|---|---|---|---|
| Elements | C % | H % | N % |
| Calculated for $C_{21}H_{26}N_2O$ (MW = 322) | 78.2 | 8.13 | 6.69 |
| Experimental | 77.8 | 8.24 | 8.51 |

IR spectrum: two bands of equal intensity are present, centered at 1699.5 cm$^{-1}$ and 1647.6 cm$^{-1}$ attributed to $v_{C=O}$ and $v_{C=N}$ respectively.

H$^1$NMR ($\delta$ shift from TMS): 1.16 (d, 12H); 2.27 (s, 3H); 2.73 (m, 2H); 2.80 (s, 3H); 7.17 (m, 3H); 7.95 (t, 1H); 8.15 (d, 1H); 8.57 (d, 1H).

Example 3
preparation of 1-{6-[2,6-diisopropylphenyl)eth-aneimidoyl]-2-pyridinyl}-1-ethanone (VII) with a ratio aniline/pyridine≅1.

The same procedure is adopted as in example 2, but using 2.70 ml (0.014 moles) of 2,6-diisopropyl aniline. At the end, the product is re-crystallized from a 1/1 vol./vol. mixture of THF/ethanol. In this way 2.4 g of a light yellow solid are obtained, having the same characteristics as that obtained in the previous example 2.

Example 4 preparation of 1-{6-[(2-t-butylphenyl)eth-aneimidoyl]-2-pyridinyl}-1-ethanone (VIII)

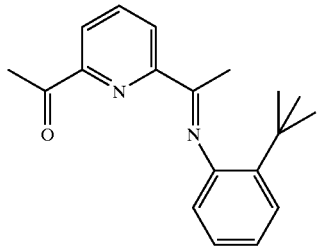

(VIII)

The same procedure is used as in example 1, but using 3.43 g of 2-tert-butyl aniline (0.023 moles) instead of 2.10 ml of aniline.

2.83 g of a light yellow solid are obtained (m.p.= 166–167° C.) corresponding to the desired product, on the basis of the following characterization:

| Elemental analysis | | | |
|---|---|---|---|
| Elements | C % | H % | N % |
| Calculated for $C_{19}H_{22}N_2O$ (MW = 294.40) | 77.5 | 7.53 | 9.52 |
| Experimental | 78.0 | 7.60 | 9.65 |

IR spectrum: two bands of equal intensity are present, centered at 1694.5 cm$^{-1}$ and 1644.5 cm$^{-1}$ attributed to $\nu_{C=O}$ and $\nu_{C=N}$ respectively.

H$^1$NMR (δ shift from TMS): 1.39 (s, 9H); 2.41 (s, 3H); 2.80 (s, 3H); 6.54 (dd, 1H); 7.24 (m, 2H); 7.43 (dd, 1H); 7.95 (t, 1H); 8.13 (d, 1H); 8.50 (d, 1H).

Example 5 preparation of 1-{6-[(2,4,6-trimethylphenyl)eth-aneimidoyl]-2-pyridinyl}-1-ethanone (IX)

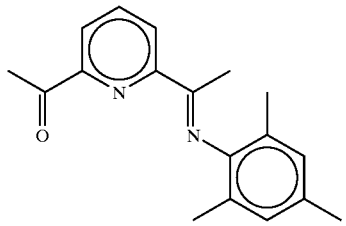

(IX)

0.937 g of 2,6-diacetylpyridine (5.70 mmoles) are dissolved in a 50 ml flask containing 9 ml of methanol. 0.80 ml of mesitylaniline (5.70 mmoles) and two drops of formic acid are then added, and the mixture is left to react at room temperature. After 16 hours the crystalline solid which has formed in the meantime, is filtered, washing with methanol.

1.2 g of a light yellow solid are obtained (m.p.=117° C.), which proves to consist of the desired product (IX), on the basis of the following characterizations:

| Elemental analysis | | | |
|---|---|---|---|
| Elements | C % | H % | N % |
| Calculated for $C_{18}H_{20}N_2O$ (MW = 280) | 77.25 | 7.2 | 10.0 |
| Experimental | 77.1 | 7.2 | 9.9 |

IR spectrum: two bands of equal intensity are present, centered at 1698 cm$^{-1}$ and 1636.8 cm$^{-1}$ attributed to $\nu_{C=O}$ and $\nu_{C=N}$ respectively.

H$^1$NMR (δ shift from TMS): 2.0 (s, 6H); 2.23 (s, 3H); 2.30 (s, 3H); 2.79 (s, 3H); 6.90 (s, 2H); 7.93 (t, 1H); 8.12 (d, 1H); 8.56 (d, 1H).

Example 6

Synthesis of the Complex {1-{6-[2,6-diisopropyl-phenyl)ethaneimidoyl]-2-pyridinyl}-1-ethanone}-cobalto-dichloride (Structure Schematized in (X))

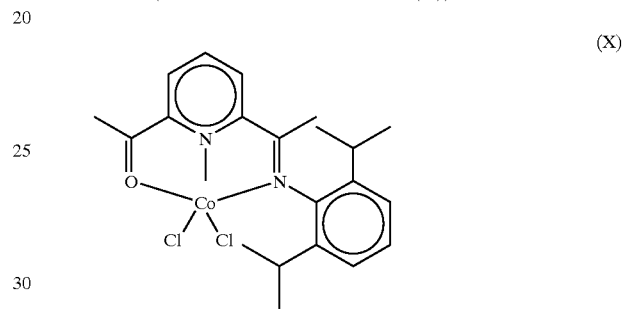

(X)

5 ml of n-butanol, 0.16 g of 2,6-acetylmono(2,6-diisopropylaniline)pyridine (0.5 mmoles), prepared as described in the previous example 2, and 0.24 g of CoCl$_2$.6H$_2$O (1.0 mmoles.) are charged into a 50 ml flask. The mixture is heated to reflux temperature for 10 minutes. On cooling a green solid precipitates, which is filtered and washed with n-butanol. 0.28 g of the desired complex are obtained.

| Elemental analysis | | | |
|---|---|---|---|
| Elements | C % | H % | N % |
| Calculated for $C_{21}H_{26}N_2OCl_2Co$ (MW = 452.3) | 55.76 | 5.75 | 6.19 |
| Experimental | 55.9 | 5.85 | 6.16 |

Example 7

Synthesis of the Complex {1-{6-[2,4,6-trimeth-ylphenyl)ethaneimidoyl]-2-pyridinyl}-1-ethanone}-cobaltdi-chloride (Structure Schematized in (XI))

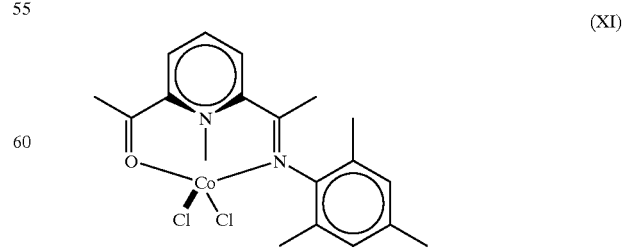

(XI)

0.35 g of CoCl$_2$.6H$_2$O (1.4 mmoles) dissolved in 30 ml of n-butanol are charged into a 50 ml flask. 0.48 g of 1-{6-[2, 4,6-trimethylphenyl)ethaneimidoyl]-2-pyridinyl}-1-ethanone (1.7 mmoles) are added. On resting at room temperature, green crystals precipitate, which are separated by filtration and washed first with n-butanol and subsequently with ethyl ether. At the end 0.40 g of crystalline solid consisting of the desired complex, are obtained.

Elemental analysis

| Elements | C % | H % | N % |
|---|---|---|---|
| Calculated for $C_{18}H_{20}N_2OCl_2Co$ MW = 409.9) | 52.69 | 4.87 | 6.83 |
| Experimental | 52.6 | 5.20 | 6.60 |

Example 8
Synthesis of the Complex {1-{6-[2,6-diisopropyl phenyl) ethaneimidoyl]-2-pyridinyl}-1-ethanone}irondichlor-ide (Structure Schematized in (XII))

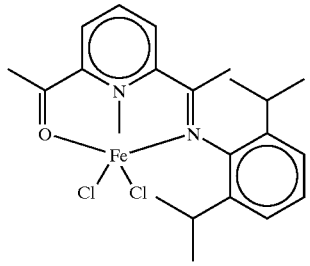

(XII)

25 ml of anhydrous THF, 0.58 g of anhydrous $FeCl_2$ and 1.47 g of 2,6-acetylmono(2,6-diisopropylaniline)pyridine (4.5 mmoles) prepared as described in example 2 above, are charged in a stream of argon into a tailed glass test-tube, equipped with a magnetic stirrer.

The mixture is left to react at room temperature for 24 hours. The solvent is removed under vacuum and a blue crystalline solid is recovered, which proves to be the desired complex.

Elemental analysis

| Elements | C % | H % | N % |
|---|---|---|---|
| Calculated for $C_{21}H_{26}N_2OCl_2Fe$ (MW = 449) | 56.14 | 5.79 | 6.24 |
| Experimental | 55.7 | 5.77 | 6.09 |

Example 9 (Comparative)
Polymerization of ethylene 0.05 mmoles of the complex [2,6-diacetylpyridine-bis(2,6-diisopropylphenylimine)]cobalt dichloride (prepared as described in example 7 of international patent application WO 98/27124, mentioned above) dissolved in 150 ml of anhydrous toluene, followed by 2.5 ml of MAO (1.57 M solution in toluene) (ratio Al/Co=80), are charged (after effecting the vacuum-nitrogen operation at least three times over a period of two hours and under static vacuum conditions), into a 300 ml volume Buchi glass autoclave, equipped with a propeller stirrer, valve for the gas inlet, thermocouple jacket and valve for charging the solutions containing the components of the catalytic system. At this point the stirring is started and the autoclave is pressurized with ethylene at 0.7 MPa, the pressure being kept constant for the whole duration of the test. The temperature increases from the initial 25° C. to 54° C. after 30 minutes. At this stage, the autoclave is depressurized and the polymerization stopped by the addition of 20 ml of methanol. The polymer is recovered by precipitation in about 600 ml of methanol acidified with HCl, filtered and dried under vacuum at 50° C. for about 8 hours.

At the end 16.5 g of polyethylene are obtained (activity 330 $g_{PE}$/mmole$_{Co}$) having the following characteristics measured by means of GPC: Mn=3580, $M_w$=11,453, $M_w/M_n$=3.2.

Example 10 (Comparative)

The same procedure is adopted and the same reagents used as in example 9 above, with the only difference that 0.025 mmoles of the complex [2,6-diacetylpyridinebis (2,6-diisopropylphenylimine)]cobalt dichloride and 0.8 ml of a solution of MAO (Al/Co=50), are charged. During the polymerization the temperature increases from the initial 29° C. to 50° C. after 30 minutes.

At the end 13.2 g of polyethylene are obtained (activity 528 $g_{PE}$/mmole$_{Co}$) having the following characteristics measured by means of GPC: $M_n$=4317, $M_w$=13,019, $M_w/M_n$=3.01.

Example 11
Polymerization of Ethylene

The same procedure is adopted as in example 9, with the only difference that 0.049 mmoles of the complex {1-{6-[2,6-diisopropylphenyl)ethaneimidoyl]-2-pyridinyl}-1-ethan-one}cobalt dichloride (obtained according to the previous example 5) and 2.5 ml of a solution of MAO (Al/Co=80), are charged. The temperature increases from the initial 25° C. to 42° C. after 30 minutes.

At the end 10 g of polyethylene are obtained (activity 150 $g_{PE}$/mmole$_{Co}$) having the following characteristics measured by means of GPC: $M_n$=1683, $M_w$=12,673, $M_w/M_n$=7.5.

Example 12

The same procedure is adopted as in example 9, with the only difference that 0.025 mmoles of the complex {1-{6-[2,6-diisopropylphenyl)ethaneimidoyl]-2-pyridinyl}-1-ethan-one}cobalt dichloride (obtained according to the previous example 5) and 0.8 ml of a solution of MAO (Al/Co=50), are charged. During the polymerization, the temperature increases from the initial 23° C. to 34° C. after 30 minutes.

5.5 g of polyethylene are obtained (activity 220 $g_{PE}$/mmole$_{Co}$) having the following characteristics measured by means of GPC: $M_n$=1862, $M_w$=15,033, $M_w/M_n$=8.1.

On comparing examples 11 and 12 described above, with comparative examples 9 and 10 respectively, representing the most pertinent of the known art consisting of international patent application WO 98/27124, it can be seen that the method according to the present invention, based on the use of mono-imine complexes having formula (VI) for polymerizing ethylene, allows the production of polymers with comparable molecular weights, and with a polymerization activity which, although lower, is still in the same order of magnitude. Considering that the preparation of the mono-imine complexes having formula (VI) is much quicker and simpler than the preparation of the corresponding bis-imine complexes, it can be appreciated that the polymerization process according to the present invention is not only original and unexpected, but is also advantageous in the context of an overall evaluation of the various elements of which it is made up. In fact, if on the one hand there is a lower, but in any case significant, activity of the complexes having formula (VI), this is compensated by a greater availability and convenience of the same complexes, with the final result that the process is all in all more convenient.

Example 13

The same procedure is adopted as in example 9, with the only difference that 0.025 mmoles of the complex {1-{6-[2,6-diisopropylphenyl)ethaneimidoyl]-2-pyridinyl}-1-ethan-one}iron dichloride (prepared according to the previous example 8) and 1.6 ml of a solution of MAO (Al/Fe 100), are charged. The temperature increases from the initial 23° C. to 30° C. after 30 minutes. At the end, 5.2 g of polyethylene are obtained (activity 208 $g_{PE}/mmole_{Co}$)

Example 14

The same procedure is adopted as in example 9, with the only difference that instead of the preformed cobalt metal complex, 0.05 mmoles of the salt Co(acetyl-acetonate)$_2$, 0.075 mmoles of ligand (2,6-diacetylpyridinemono(2,6-di-i-propylanilineimine)] are cha-rged to promote the formation in situ of the active complex. 1.24 ml of a solution of MAO (Al/Co=80) are subsequently charged, with the function of activator. The temperature increases from the initial 24° C. to 30° C. after 30 minutes. 2.6 g of polyethylene are obtained (activity 52 $g_{PE}/mmole_{Co}$) having the following characteristics measured by means of GPC: $M_n$=1964, $M_w$=16,495, $M_w/M_n$=8.4.

What is claimed is:

1. A complex of a metal M selected from transition metals and lanthanides, having the following formula (VI):

$$(IAP)M(X)_n \qquad (VI)$$

wherein:

M is a metal selected from transition metals, i.e. metals of groups 3 to 12 of the periodic table, and from lanthanides, which is in an oxidation state "s" positive and different from zero;

each X is independently a group of an anionic nature bound to the metal as anion in an ionic couple or with a covalent bond of the "σ" type;

"n" expresses the number of X groups sufficient for neutralizing the formal "+s" charge of the metal M, and is equal to "s" if all the X groups are monovalent; and (IAP) represents a neutral organic ligand;

characterized in that said ligand (IAP) consists of a mono-imine of 2,6-diacylpyridine having the following general formula (V):

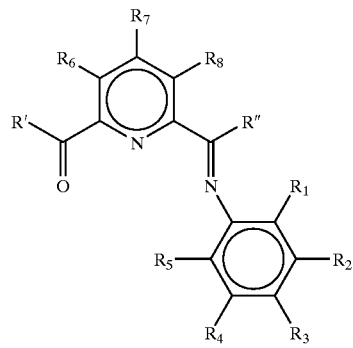

wherein:

R' and R" are independently hydrogen or a hydrocarbon radical, preferably aliphatic, having from 1 to 10 carbon atoms, optionally halogenated, more preferably methyl;

each $R_i$ (i=1–8) is independently hydrogen, halogen or $C_1$–$C_{10}$ alkyl, or $C_6$–$C_{15}$ aryl, optionally halogenated, on the condition that at least one of the $R_1$ or $R_5$ groups, preferably both, is a hydrocarbon radical.

2. The complex having formula (VI) according to claim 1, wherein said "s" oxidation state of said metal M is between 1 and 4.

3. The complex having formula (VI) according to claim 1, wherein said metal M is selected from metals of groups 8 and 9 of the periodic table, preferably from Fe, Co, Ru, Rh and Ir in oxidation state "s"=+2.

4. The complex having formula (VI) according to claim 1, wherein, in said ligand (IAP) having formula (V), $R_1$ and $R_5$ are both methyl or ethyl, or at least one of these is a branched alkyl group having from 3 to 10 carbon atoms.

5. The complex having formula (VI) according to claim 4, wherein said $R_1$ and $R_5$ groups are both isopropyl, s-butyl, t-butyl, cyclohexyl or benzyl.

6. The complex having formula (VI) according to claim 1, wherein said ligand $(X)_n$ of an anionic nature is selected from halides, especially chloride and bromide, sulfates and acid sulfates, alkyl- and aryl-sulfonic groups, phosphates and polyphosphates, alkyl- and aryl-phosphonic groups, hydride, linear, cyclic or branched alkyl groups having from 1 to 15 carbon atoms, alkylsilyl groups having from 1 to 20 carbon atoms, aryl groups having from 6 to 15 carbon atoms, alkoxyl or thioalkoxyl groups having from 1 to 10 carbon atoms, carboxylate or dicarboxylate groups having from 1 to 10 carbon atoms, a dialkylamide or alkylsilylamide group having from 2 to 15 carbon atoms.

7. A catalytic system for the (co)polymerization of α-olefins comprising at least the following two components, as such or combined with each other:

(A) a complex having formula (VI) of a metal M selected from transition metals and lanthanides, according to claim 1;

(B) a co-catalyst consisting of at least one organic compound of an element M' different from carbon and selected from the elements of groups 2, 12, 13 or 14 of the periodic table.

8. The catalytic system according to claim 7, wherein said element M' in the co-catalyst (B) is selected from the group consisting of boron, aluminum, zinc, magnesium, gallium and tin.

9. The catalytic system according to claim 7, wherein said co-catalyst (B) is a linear or cyclic, polymeric aluminoxane.

10. The catalytic system according to claim 9, wherein the atomic ratio between aluminum in the aluminoxane which forms the co-catalyst (B) and the metal M in the complex having formula (VI) which forms component (A), ranges from 100 to 5000.

11. The catalytic system according to claim 7, wherein said co-catalyst (B) consists of at least one compound or a mixture of organometallic compounds of boron capable of reacting with the complex having formula (VI) by extracting from this a σ-bound ligand X as defined above, to form on the one hand at least one neutral compound, and on the other hand an ionic compound consisting of a cation containing the metal M coordinated to the ligand (IAP), and an organic non-coordinating anion containing the metal M', whose negative charge is delocalized on a multicentric structure.

12. The catalytic system according to claim 11, wherein the atomic ratio between the boron atom in component (B) and the atom M in the complex having formula (VI) ranges from 0.5 to 10.

13. The catalytic system according to claim 11, wherein said ligand X in the compound having formula (VI) is different from alkyl, and said co-catalyst (B) comprises, in addition to said ionic compound of the metal M', an alkylating agent consisting of an aluminum alkyl or an aluminum alkylhalide having from 1 to 8 carbon atoms in each alkyl residue.

14. A process for the (co)polymerization of α-olefins, either in continuous or batchwise, in one or more steps, at low (0.1–1.0 MPa), medium (1.0–10 MPa) or high (10–150 MPa) pressure, at temperatures ranging from 20° to 250° C., optionally in the presence of an inert diluent, characterized in that at least one α-olefin is put under the above conditions in contact with a catalytic system according to claim 7.

15. The (co)polymerization process according to claim 14, carried out in the presence of an inert liquid consisting of an aliphatic or cycloaliphatic or aromatic hydrocarbon having from 3 to 8 carbon atoms, wherein said α-olefin comprises from 2 to 20 carbon atoms and said metal M of the compound having formula (VI) in said catalytic system, has a concentration ranging from $10^{-8}$ to $10^{-4}$ moles/liter.

16. The (co)polymerization process according to claim 14, wherein said α-olefin is ethylene or a mixture of ethylene with a different polymerizable unsaturated monomer.

17. The (co)polymerization process according to claim 14, wherein said catalytic system comprises a co-catalyst B which is a linear or cyclic, polymeric aluminoxane.

18. The catalytic system according to claim 7, wherein said elements M' in the co-catalyst (B) is selected the group consisting of boron and aluminum.

19. The catalytic system according to claim 7, wherein said element M' in the co-atalyst (B) is boron.

20. The catalytic system according to claim 7, wherein said element M' in the co-catalyst (B) is aluminum.

* * * * *